United States Patent [19]

Taub

[11] Patent Number: 5,059,271
[45] Date of Patent: Oct. 22, 1991

[54] METHOD OF SUPPORTING AND RETAINING SURGICAL INSTRUMENTS ON A NON-SKID SUPPORTING SURFACE

[76] Inventor: Stanley Taub, 465 W. Broadway, New York, N.Y. 10012

[21] Appl. No.: 45,764

[22] Filed: Apr. 27, 1987

Related U.S. Application Data

[63] Continuation of Ser. No. 861,121, May 7, 1986, abandoned, which is a continuation of Ser. No. 712,317, Mar. 13, 1985, abandoned, which is a continuation of Ser. No. 403,083, Jul. 29, 1982, abandoned.

[51] Int. Cl.$^5$ .............................................. C09J 5/00
[52] U.S. Cl. ................................... 156/306.3; 106/36; 128/132 D; 128/DIG. 21; 156/152; 156/344; 248/346; 269/289 R; 269/909; 427/2; 428/141; 428/447
[58] Field of Search ..................... 156/152, 306.3, 249, 156/306.6, 313, 329, 60, 344, 247; 427/2, 208.4; 106/36; 524/588; 248/346; 269/289 R, 909; 128/132.8, 816.21; 428/141, 355, 266, 447

[56] References Cited

U.S. PATENT DOCUMENTS

| | | | |
|---|---|---|---|
| 3,146,799 | 9/1964 | Fekete | 524/588 |
| 3,236,370 | 2/1966 | Pereny et al. | |
| 3,460,975 | 8/1969 | Stebleton | 427/2 |
| 3,882,859 | 5/1975 | Ericson | |
| 3,916,887 | 11/1975 | Kelly | 128/132 D |
| 4,061,709 | 12/1977 | Miller et al. | |
| 4,192,494 | 3/1980 | Mima | 428/141 |
| 4,395,451 | 7/1983 | Althouse | 428/141 |

Primary Examiner—John J. Gallagher

[57] ABSTRACT

A method of using a sheet of silicone rubber with one smooth, tacky side as a non-slip surface for one or more articles. The sheet is placed on the surface of an object, and articles to be supported are placed on the smooth, tacky side of the sheet. The articles will not slide off the sheet despite inclination or movement of the object surface.

8 Claims, 2 Drawing Sheets

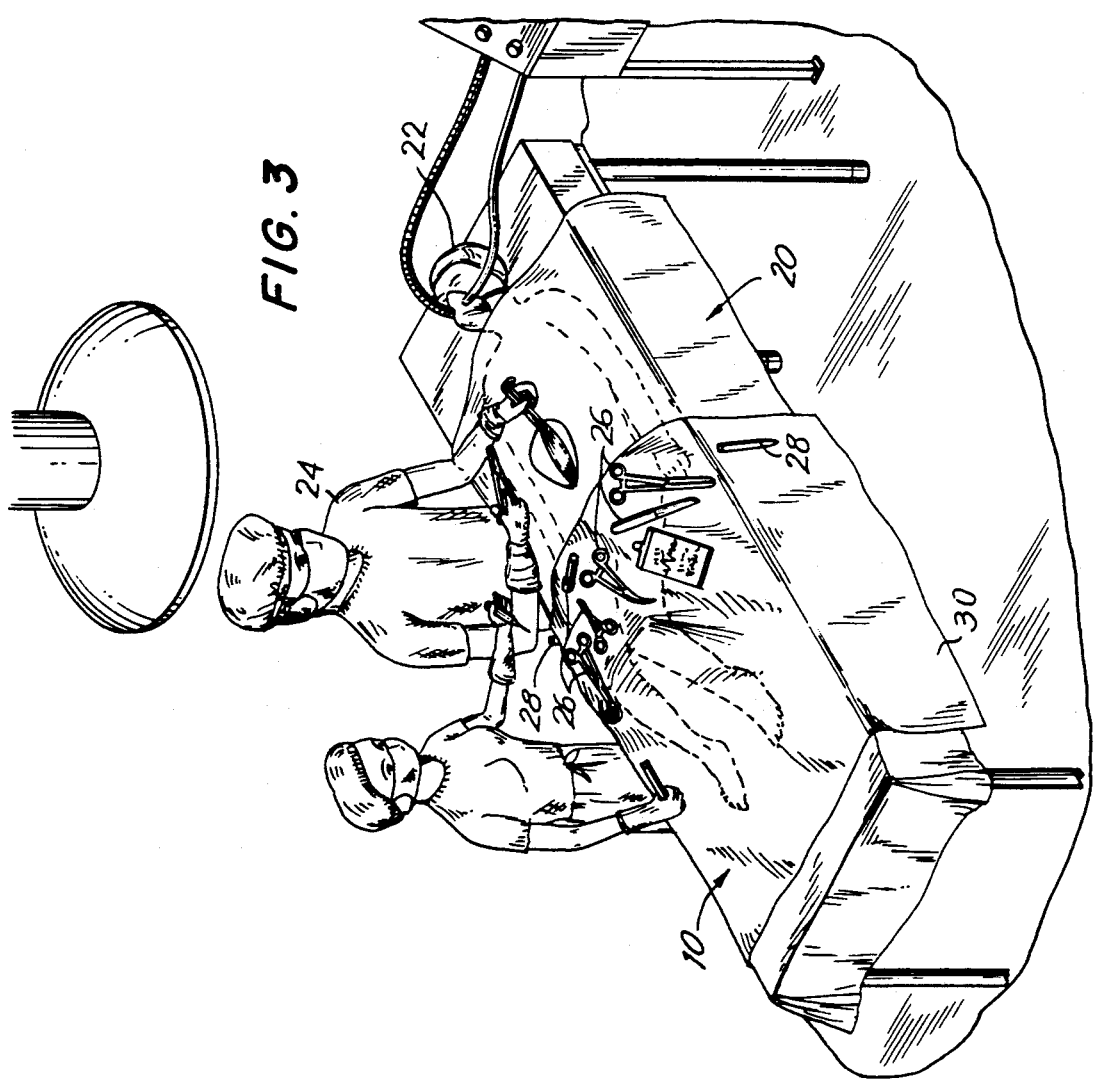
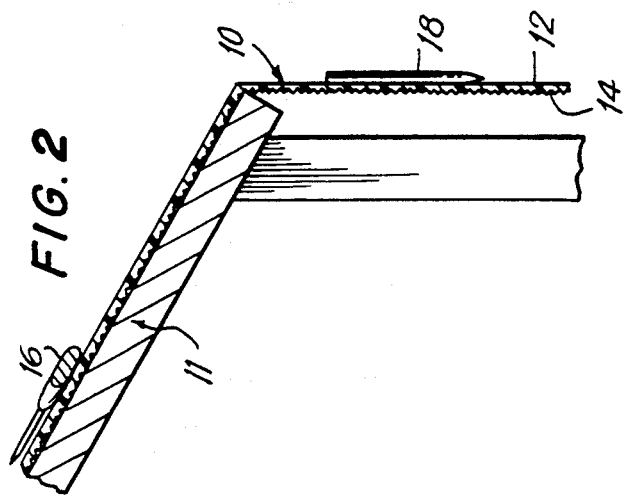

METHOD OF SUPPORTING AND RETAINING SURGICAL INSTRUMENTS ON A NON-SKID SUPPORTING SURFACE

CROSS REFERENCE TO RELATED APPLICATIONS

This application is a continuation of application Ser. No. 861,121, filed on May 7, 1986 now abandoned, which is a continuation of application Ser. No. 712,317, filed Mar. 13, 1985, now abandoned, which is a continuation of application Ser. No. 403,083, filed on Jul. 29, 1982 also abandoned.

TECHNICAL FIELD

The present invention relates to a method of using a sheet material composed of methyl vinyl polysiloxane as a supporting surface for articles, particularly surgical instruments, which articles due to the surface properties of the sheet material will not slide off the sheet material when it is inclined, agitated or otherwise disturbed.

BACKGROUND ART

The need for a non-skid surface upon which articles may be placed has been recognized in the art. Thus, the prior art discloses a variety of non-skid supporting surfaces upon which articles, such as tools and the like, may be placed. Such prior art non-skid surfaces are constructed, for example, from materials possessing non-skid surface properties or by embossing or texturing materials having normally smooth slippery surfaces.

There is a special need for non-skid supporting surfaces in the field of medicine, particularly, surgery, upon which a surgeon may place surgical instruments while performing surgery. This special need has also been recognized in the prior art. For example, U.S. Pat. No. 3,882,859 discloses a surgical drape with a large fenestration. The surgical drape is covered by a thin elastomeric sheet, having a high elastic modulus and high coefficient of friction. In use, the drape rests directly upon the body of the patient, immediately on or adjacent to the operative site, and provides a sterile, non-skid resting place for instruments adjacent to the operative site.

While this drape and others like it are constructed of materials having relatively high coefficients of friction, the coefficients of friction of these materials are not sufficiently high to prevent surgical instruments from sliding off the drape when it is at a sharp incline, for example 45° or more, or when it is agitated or otherwise disturbed during the operation. This may be due to the fact that while many elastomeric materials have relatively high coefficients of static friction they have relatively low coefficients of kinetic friction.

Another disadvantage of such prior art drapes is that the elastomeric materials from which the drapes are made do not allow instruments to be dropped thereon without the fear that the instruments will fall off the drape Still another disadvantage is that such drapes cannot be washed during use.

Another type of surgical drape which is employed is a "magnetic drape". Magnetic drapes, as the name implies, have magnets distributed between the top and bottom surfaces of the drape for holding metallic instruments in place. These drapes, however, have many disadvantages. Thus, the magnets which are positioned between the top and bottom surfaces of the drape tend to break through the drape after repeated sterilization. Such drapes are also difficult to use because they are stiff and heavy and require precise placement of instruments over the magnets. Another disadvantage is that the magnets in the drape magnetizes the instruments. Still another disadvantage is that such drapes are not useful in holding non-magnetizable articles.

Accordingly, it is one of the objects of the present invention to provide a non-skid surface for supporting articles such as tools, surgical instruments and the like.

It is another object of the present invention to provide a sheet material having a sterile, permanently tacky surface made without sticky adhesives, and having high coefficients of both static and kinetic friction. Such a sheet material may be placed near the operating area. All types of surgical instruments may be placed or dropped upon it and surgical instruments will not slide from it when the surface is at an incline, agitated or otherwise disturbed.

It is still another object of the present invention to provide a reuseable sterile material which may be repeatedly autoclaved or gas sterilized without losing its properties.

SUMMARY OF THE INVENTION

It has been found in accordance with the present invention that a sheet material composed of methyl vinyl polysiloxane containing a small amount of ground silica filler may be employed as a supporting surface for articles, such as surgical instruments. The sheet material according to the present invention has two sides, one side having a permanently tacky surface and the other side having a textured or embossed surface. The tacky surface is formed during the curing process, which is described in detail hereinafter, and not from a sticky adhesive. The tacky surface has high coefficients of both static and kinetic friction, which may be attributable to the tacky quality of the surface.

In use, the sheet material is placed on a surface with its tacky surface facing upward. Articles such as tools and surgical instruments may then be placed on the tacky surface of the sheet material. Due to the surface takiness and high coefficients of both static and kinetic friction of the material, articles will not slide off the surface when it is inclined (up to about 90° slope), agitated, or otherwise disturbed.

The sheet material according to the present invention is particularly useful as a supporting surface for surgical instruments. When used in this manner the sheet material of the instant invention is normally placed on top of a surgical drape in a convenient location with its tacky surface facing upward. During the operation, the doctor may place surgical instruments on the sheet material. Due to the tackiness and high coefficient of friction of the sheet material, surgical instruments will not slip or slide off the sheet material. Moreover, surgical instruments which are dropped on the sheet material will not slip off, but rather will remain on the sheet material at the place where they are dropped. The sheet material may also be reused since as it can be repeatedly sterilized by any standard technique without losing its properties, particularly its tacky surface property.

BRIEF DESCRIPTION OF DRAWINGS

FIG. 2 is a cross sectional view of the sheet material of FIG. 1 taken through line 2—2.

FIG. 3 is a perspective view of the sheet material being used at the operating table as a supporting surface for surgical instruments.

BEST MODE FOR CARRYING OUT THE INVENTION

Figure 1:
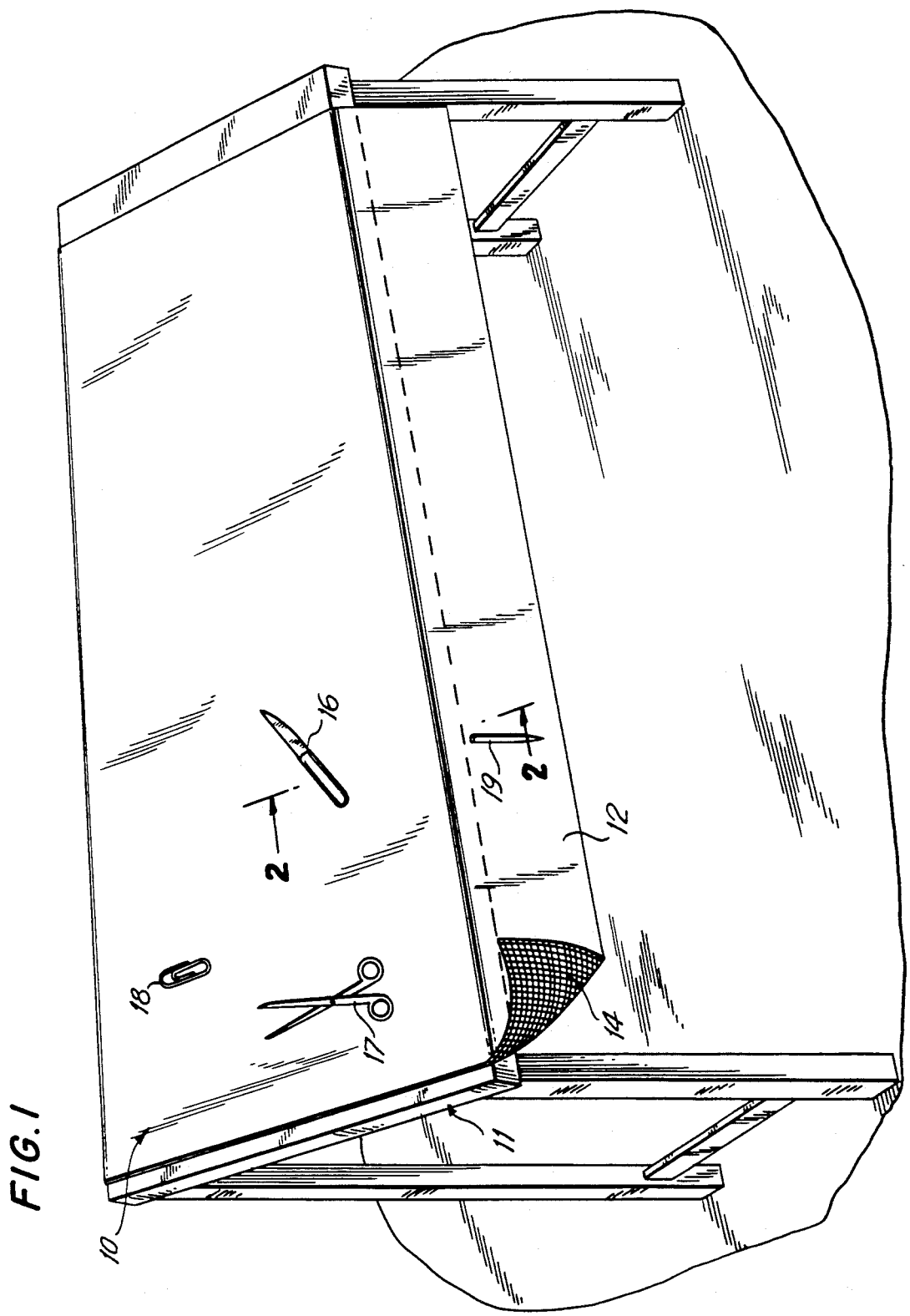
FIG. 1 is a perspective view showing the sheet material of the instant invention positioned on an inclined surface and having articles positioned thereon.

As described hereinabove, the instant invention relates to the use of a sheet material composed of methyl vinyl polysiloxane containing a small amount of ground silica filler.

As presently preferred, the sheet material of the present invention is formed by the following process. The process comprises forming a sheet material from methyl vinyl polysiloxane containing a small amount of ground silica, for example, from 10 to 50 parts per 100 parts of methyl vinyl polysiloxane. The sheet material preferably contains of from about 15 to 30 parts of ground silica per 100 parts of polysiloxane. The material is formed into a sheet by calendering it onto a fabric carrier. While the formed sheet material is on the fabric carrier, it is cured with an organic peroxide. It is presently preferred to employ 2,4 dichlorobenzoyl peroxide, although any suitable peroxide may be used. As a result of this curing technique, the surface of the sheet material exposed to the air, while on the fabric, becomes tacky and the surface of the sheet material in contact with the fabric becomes textured due to the embossments on the fabric. At this point in the process, the sheet material is passed through a hot air oven and the tacky quality of the air exposed surface of the sheet material becomes permanent. Thereafter, the sheet material is cut into the desired shape and size. The sheet material may be cut into any desired shape and size depending upon the end use of the material. Examples of some preferred end uses will be described hereinafter.

The properties of the resultant sheet material of the instant invention are shown in Table I below:

TABLE I

| | |
|---|---|
| color | blue |
| thickness | 0.03 inch +/− about 0.005 inch (ASTM 0412) |
| | durometer Shore A-30 + 10-5 (ASTM 2240) |
| strength | minimum, 600 lbs./sq. inch (ASTM 412) |
| elongation | minimum, 400% (ASTM 412) |
| sufrace tack | minimum, 20 gm. as tested on a POLYKEN PROBE TACK tester, Model No. 480-2, from TESTING MACHINE, INC., Amityville, New York. Average of ten readings using a 20 gm. weight and a one-half second dwell time. |
| useful temperature range | −100° to 500° F. |
| physical characteristics | a smooth tacky surface and a rough textured surface |
| coefficient of static friction | 1.19 |
| coefficient of kinetic friction | 1.00 |

The coefficients of friction were determined in accordance with ASTM-D-1894-78 (Part 35) 1980 test.

Referring now to FIGS. 1-3 in detail, the preferred sheet material according to the present invention is generally designated by reference numeral 10. As illustrated in FIGS. 1 and 2, the sheet material 10 has a smooth tacky surface 12 and a rough textured surface 14. As shown, the sheet material 10 is positioned on an inclined surface 11. The textured surface 14 acts to hold the sheet material on the inclined surface 11. A knife 16, scissors 17, paper clip 18 and pencil 19 are positioned on the sheet material 10. Because of the tacky surface quality of the sheet material, the articles 16, 17, and 19 will not slip or slide off the surface even though it has approximately a 60° slope In fact, the pencil 19, which is positioned on the portion of the sheet material 10 which overhangs the surface 11, will not slip or slide off the sheet material 10 even though it is at about a 90° slope. To obtain even better adherence to the sheet material 10, the articles 16, 17, 18 and 19 may be pressed against the tacky surface 12.

Referring to FIG. 3, the preferred use for the sheet material 10 is illustrated. As depicted, the sheet material 10 is placed over a portion of a surgical drape 20 which is covering a patient 22 who is being operated upon. The doctor 24 may then place surgical instruments 26 and 28 on the sheet material 10. These instruments may include metallic and non-metallic instruments such as a scalpel, clamps, scissors, plastic suction tubes and plastic pens. As shown, even though a portion 30 of the sheet material 10 overhangs the operating table at an angle of about 90°, surgical instruments 28 will not slip or slide off the sheet material 10. When used in this manner, the sheet material may have any suitable dimensions. However, it is presently preferred that the sheet material have a width of about nineteen inches and a length of about twenty-four inches.

If during the operative procedure a significant portion of the tacky surface becomes covered with lint, powder, dried blood or fatty tissue, the holding capability of the sheet material may be reduced, but it can be immediately restored by rinsing or gently washing the tacky surface with a wet sponge. In addition, since the sheet material 10 is heat resistant up to 500° F., it may be sterilized and reused. Moreover, the supporting surface 12 will retain its tackiness when wet.

While not illustrated in the drawings, the sheet material may be used in a variety of ways to support various other articles. For example, a precut piece of the sheet material according to the present invention may be placed on a tray for use on a boat, airplane or other vehicle to hold articles such as plates, cups, saucers, cutlery and the like in place.

A precut piece of the sheet material of the instant invention may also be used, for example, as a supporting surface for tools when working on the contoured surface of an automobile. Thus, the sheet material may be placed over the portion of the car being worked upon and tools and other implements can be placed thereon. The sheet material will protect the car from damage caused by the tools and will keep the tools in place.

The sheet material of the present invention may also be used as a supporting surface for movie film during the editing process. Because of the sheet material's tacky surface, the film is held vertically in place without the need for supporting pins, which are employed in conventional film editing.

It will, of course, be recognized that the sheet material of the instant invention may have many other similar uses as a supporting surface for still other articles.

While I have herein shown and described the preferred embodiments of the present invention and have suggested certain modifications thereto, it will be apparent that further changes and modifications may be made without departing from the spirit and scope of the invention. Accordingly, the above description should be construed as illustrative and not in the limiting sense, the scope of the invention being defined by the following claims.

What is claimed is:

1. A method of supporting and retaining surgical instruments on a surface which is at least in part not flat or horizontal, comprising:

forming a flexible sheet of predetermined dimensions from methyl vinyl polysiloxane containing small amounts of ground silica filler, said sheet having two sides, one side being smooth, said smooth side having an inherently tacky surface of the type that is formed when the polysiloxane is cured with said smooth side exposed to air, and having relatively high kinetic and static coefficients of friction;

placing said sheet on said surface with said smooth tacky side of said sheet facing upwardly; and placing a surgical instrument on said smooth tacky surface whereby said instrument is supported thereon and does not slip or slide therefrom.

2. The method according to claim 1, wherein the other side of said sheet has a textured surface.

3. The method according to claim 1, wherein said sheet of methyl vinyl polysiloxane has a thickness of from about 0.025 inch to about 0.035 inch.

4. The method according to either claim 1 or 2 wherein said surface is the surface of a surgical drape overlying a patient and wherein said sheet may be subjected to washings and sterilization without substantial loss of its inherent tacky surface qualities.

5. The method according to claim 1, wherein said instrument is pressed against said smooth tacky side.

6. The method according to claim 1, wherein said surface is inclined at a slope of greater than 30°.

7. The method according to claim 5, wherein said surface is inclined at a slope of about 90°.

8. The method according to claim 1, wherein the ground silica filler is present in an amount of from about 10 to about 50 parts per 100 parts of methyl vinyl polysiloxane.

* * * * *